United States Patent [19]

Snee

[11] 4,348,888
[45] Sep. 14, 1982

[54] EXPLOSIMETER

[75] Inventor: Timothy J. Snee, Buxton, England

[73] Assignee: National Research Development Corporation, London, England

[21] Appl. No.: 192,938

[22] Filed: Oct. 1, 1980

[30] Foreign Application Priority Data

Oct. 11, 1979 [GB] United Kingdom ............... 7935394

[51] Int. Cl.³ .............................................. G01N 31/12
[52] U.S. Cl. .......................................... 73/23; 422/98
[58] Field of Search ............. 73/23; 23/232 R, 232 E, 23/230 PC; 422/83, 98

[56] References Cited

U.S. PATENT DOCUMENTS 3,447,359 6/1969 Kapff ........................................ 73/23
3,943,775 3/1976 DeBaun ................................... 73/23

FOREIGN PATENT DOCUMENTS 2253411 6/1975 France .
2330288 5/1977 France .
1442742 7/1976 United Kingdom .
2013884 8/1979 United Kingdom .

Primary Examiner—Stephen A. Kreitman
Attorney, Agent, or Firm—Cushman, Darby & Cushman

[57] ABSTRACT

The explosibility of an atmosphere which may contain a combustible gas or vapor or mist or aerosol is sensed by drawing a known volume of the atmosphere through a filter (14) and into a container (16); in a safe environment drawing the sample through the filter which is heated; completely oxidising any combustible material present; and sensing the quantity of oxygen required for complete combustion. The concentration of combustible material as a percentage of the lower explosive limit can be approximately determined even when the combustible material is unknown.

11 Claims, 5 Drawing Figures

EXPLOSIMETER

PREAMBLE

This invention relates to a method and apparatus for determining the explosibility of a combustible mixture. A fuel/air mixture is explosible if its concentration lies between the upper and the lower flammability limits. In practical situations any concentrations above the lower limit should be considered dangerous as concentration above the upper limit, while not immediately flammable, are highly likely to mix with air and become flammable. Thus the hazard of a fuel/air mixture can be assessed by measuring the fuel concentration as a percentage of the lower explosive limit.

Conventional explosimeters which determine explosibility are usually specific to one gas; combustible gases widely different in chemical structure give different readings at the lower explosive limit. Alternatively, different explosive gases can be sensed by one instrument, but the gas must be identified before testing so that an appropriate instrument setting can be used. Further, such detectors are sensitive only to gases and may give totally misleading readings, on a fail-dangerous basis, if used to sense an explosive mist, aerosol or vapour. Yet another problem is that conventional devices may only operate up to the lower or sometimes the upper explosive limit, and therefore cannot detect potentially dangerous concentrations above the upper explosive limit.

It is always convenient and often essential for an explosimeter to be portable. It must therefore be safe for use in explosive atmospheres, which places severe restrictions on its design.

In the improved method for sensing explosive atmospheres according to the invention, gases, vapours, mists and aerosols can all be sensed, even up to concentrations well above the upper explosive limit, and the constituents need not be identified. The apparatus is designed with safety requirements in mind.

BRIEF SUMMARY OF THE INVENTION

According to the invention, a method of sensing the explosibility of an atmosphere which may contain a combustible gas or vapour or mist or aerosol comprises drawing a known volume of the atmosphere through a filter on which any condensible material condenses and into a container;

in as safe environment, establishing a steady flow of oxygen-containing gas through a combustion chamber and past an oxygen sensor, heating the filter and drawing the gas sample from the container through the heated filter as part of the steady gas flow through the combustion chamber so that any combustible material is completely oxidised causing a decrease in oxygen concentration in the gas flow;

sensing and integrating any such decrease, and from the integrand determining the explosibility of the known volume.

The decrease in oxygen concentration gives a measure of the quantity of oxygen required to oxidise any combustible gas or mist etc., present in the known volume sample. For a stoichiometric fuel concentration $C_{st}$ the quantity of oxygen required to oxidise the fuel will equal to that in the known volume sample and for actual concentrations $C_{act}$ greater or less than stoichiometric a proportional quantity of oxygen will be required. Thus by measuring the volume of oxygen consumed it is possible to measure fuel concentration directly in terms of the stoichiometric fuel concentration i.e.

$$\text{integrand} = KC_{act}/c_{st}$$

where K is a constant. It is known that the ratio of stoichiometric concentration to the concentration at the lower explosive limit $C_{lel}$ is approximately constant and is about 0.5 for most fuels, i.e.

$$C_{lel}/C_{st} \approx 0.5$$

Thus the flammability or explosibility can be determined by measuring the ratio of the actual fuel concentration to the stoichiometric fuel concentration, i.e.

$$\text{percentage of l.e.l.} = \frac{C_{act}}{C_{lel}} \times 100\% = \frac{C_{act}}{C_{st}} \times \frac{C_{st}}{C_{lel}} \times 100\%$$

$$\frac{C_{act}}{C_{st}} \times 2 \times 100\%$$

$$\text{integrand} \times 2K \times 100\%$$

The method according to the invention is intended as a warning device and is not required to measure precisely the concentration of combustible material; the approximation is therefore tolerable. However, where the composition of the fuel is known a more accurate comparison can be made between measured fuel concentration and the known limits of flammability.

The oxygen-containing gas may be the earth's atmosphere at a safe environment remote from the atmosphere under test and to which the sample container and filter are removed. The oxygen-containing gas in the steady flow preceding arrival of exhaust gas from the sample at the oxygen sensor will be the atmosphere initially contained in the apparatus, i.e in the combustion chamber and connecting tubes. The oxygen-containing gas in the steady flow succeeding arrival of the sample exhaust gas at the oxygen sensor may be the atmosphere of the safe environment which is drawn into and through the sample container as the sample is drawn through the heated filter.

To determine the integrand, the output of the oxygen sensor which will be a voltage proportional to oxygen concentration, is converted to a pulse train with frequency proportional to voltage at a first proportional rate, and pulses are counted for a period T during which no exhaust gas from the sample reaches the sensor. For a subsequent, longer period such as 4T, during which all of the sample exhaust gas passes the sensor, the voltage output is converted at a second proportional rate, in this case one quarter of the first rate, and pulses are subtracted from the total. If no fuel is present, the final count is zero. Any count above zero corresponds to the presence of an oxidisable material in the sample.

The invention also extends to apparatus for carrying out the method.

BRIEF DESCRIPTION OF THE DRAWINGS

The invention will now be described with reference to the accompanying drawings in which.

DESCRIPTION OF THE DRAWINGS

Figure 1:
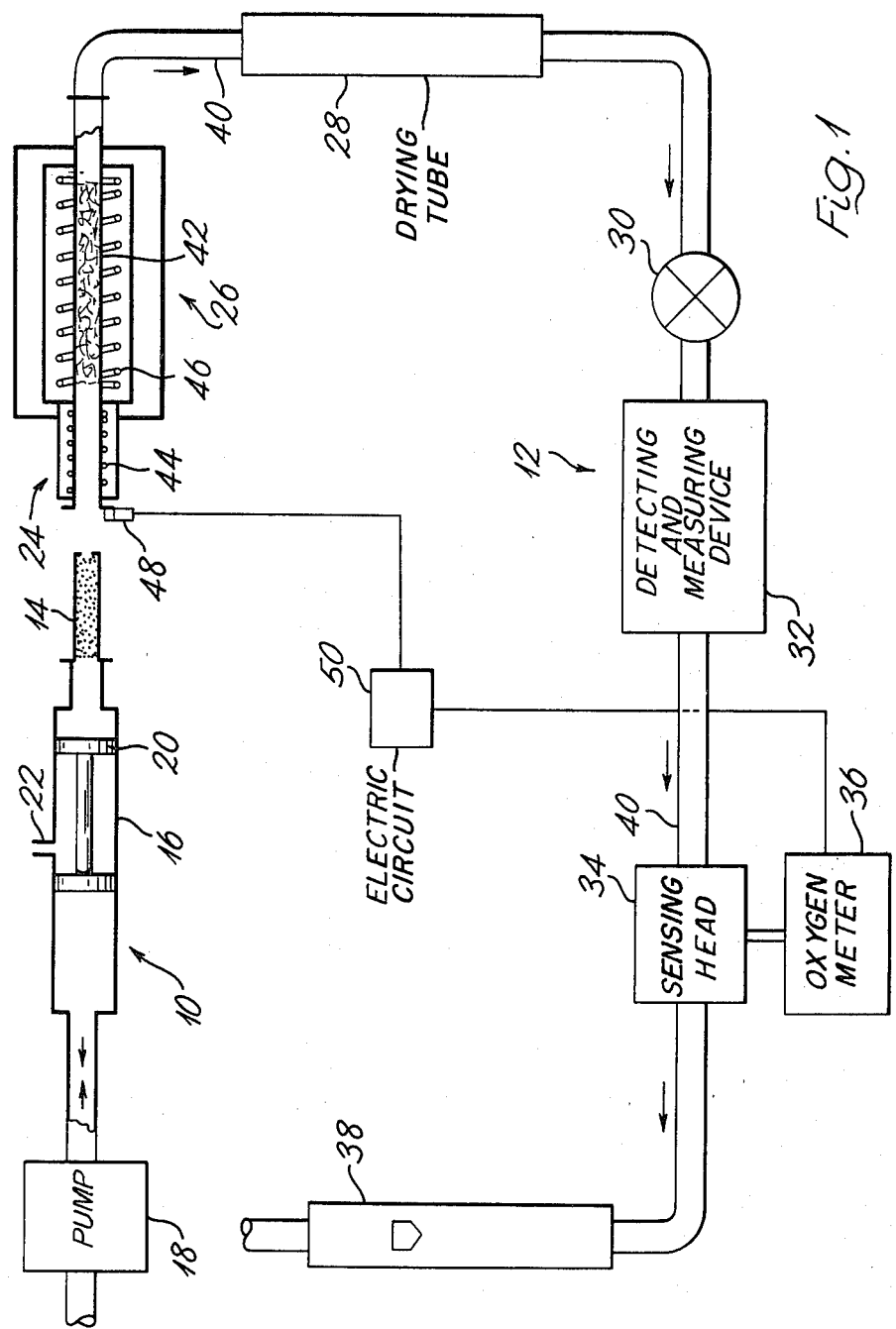
FIG. 1 is a schematic diagram of two-part explosimeter according to the invention.

In FIG. 1, the apparatus is shown in two parts, a portable sample collecting device indicated generally as reference 10, and a detecting and measuring device indicated generally as reference 12 which will be at a position remote from the possibly explosive atmosphere.

The collecting device 10 consists of a filter 14 in the form of a steel tube containing compacted steel wool. One end of the tube is connected to the input end of a cylindrical sample container 16, the output end of which is connected to a spark-free two-way pump 18. In the container 16 is a double-ended piston 20 and at the centre point of the piston traverse there is an air inlet tube 22.

The detecting and measuring device 12 consists of a filter heater 24, a catalytic reactor 26, a drying tube 28, a needle valve 30, a pump 32, a sensing head 34 of an oxygen meter 36 and a rotameter 38, connected in series by connecting tubes 40.

The filter heater 24 and reactor 26 are formed by adjacent portions of a stainless steel tube 42. The outer, filter heater end is surrounded by a first heating coil 44, and the inner, reactor end is surrounded by a second heating coil 46 and contains a platinised alumina catalyst supported on rock wool. The reactor is insulated. The oxygen meter 34, 36 can be based on a polarographic oxygen sensor, for example a Draeger oxygen meter E12.

In use, the collecting device, with the piston 20 fully towards the filter end of the container 16, is taken to the atmosphere to be tested, either the whole device or the filter 14 inserted into the atmosphere, and the pump 18 is operated to draw a sample of the atmosphere through the filter 14 into the container, the piston moving to the left in the Figure. The collecting device is then removed from the vicinity of the suspect atmosphere. With the piston at the left-hand end, the air inlet hole 22 is connected to the part of the container which contains the sample; the size of the inlet 22 is chosen so that diffusion through it is negligible, considering the length of time the sample is to be stored.

The collecting device 10 is then taken to the detecting device 12 which is situated at a safe, remote position. The heating coils 44, 46 are switched on and allowed to reach equilibrium, the filter 14 is inserted in the filter heater, and the pump 32 is operated to draw the gas sample from container 16 through the heated filter 14 into the reactor 26, together with condensed material which revapourises from the filter, and air which passes through the inlet 22. The piston 20 remains at the left-hand end of the container 16. The sample plus air is pumped through the reactor, which is designed so that any combustible material is completely oxidised, and the exhaust gases plus excess oxygen pass to the sensing head 34. Flow rate is measured by the rotameter 38.

The sample from the collecting device 10 does not pass to the catalytic reactor 26 as a block of gas; due to turbulence and mixing in the container with air drawn through the inlet, the sample is diluted with air. However, if there is any combustible material in the sample, its oxidation will cause a decrease in oxygen concentration, and by integration of the amount of oxygen consumed, the amount of combustible material in the known sample volume can be calculated. A stoichiometric fuel concentration, i.e. the balanced mixture of fuel and oxygen which would give complete combustion with no excess oxygen, gives an integrated oxygen consumption which is approximately independent of the type of combustible material and depends only on sample volume. Thus by drawing in a known sample volume it is possible to obtain a direct measure of the ratio of the actual fuel concentration in the sample to the stoichiometric fuel concentration. As explained above, this ratio is proportional to explosibility. For a known combustible material, a precise conversion factor can be applied, but for any unknown combustible material, the conversion factor will be approximately the same, so that a method according to the invention can be applied to derive the approximate explosibility of an unknown material.

Thus a measure of the integral decrease in oxygen over the period during which the combustible material in the sample is passing through the reactor can give a direct measure of the explosibility of the sample. It has already been stated that the object is not a precise measure, but an indication of a dangerous or potentially dangerous atmosphere.

Since the sample material does not pass through the reactor 26 as a plug, but is mixed with oxygen and passes over an extended period, measurement of oxygen concentration in the exhaust gases must be made over a period sufficiently long to sense all of the decrease due to combustion. This period must be determined in accordance with sample volume and flow rate.

In industrial environments, the actual oxygen concentration in the ambient atmosphere may be less than the normal 21%. It is therefore convenient to provide a correct measure of this concentration at the time of the measurement. In the apparatus according to the invention the atmosphere contained in the reactor 26 and connecting tubes 40 is used to give this measure. Insertion of the filter in the filter heater 24 operates a switch 48 connected to a suitable electronic circuit 50 which is connected to the oxygen meter 36. The ambient concentration of oxygen is thus established before any products of combustion reach the sensing head 34.

Figure 2:
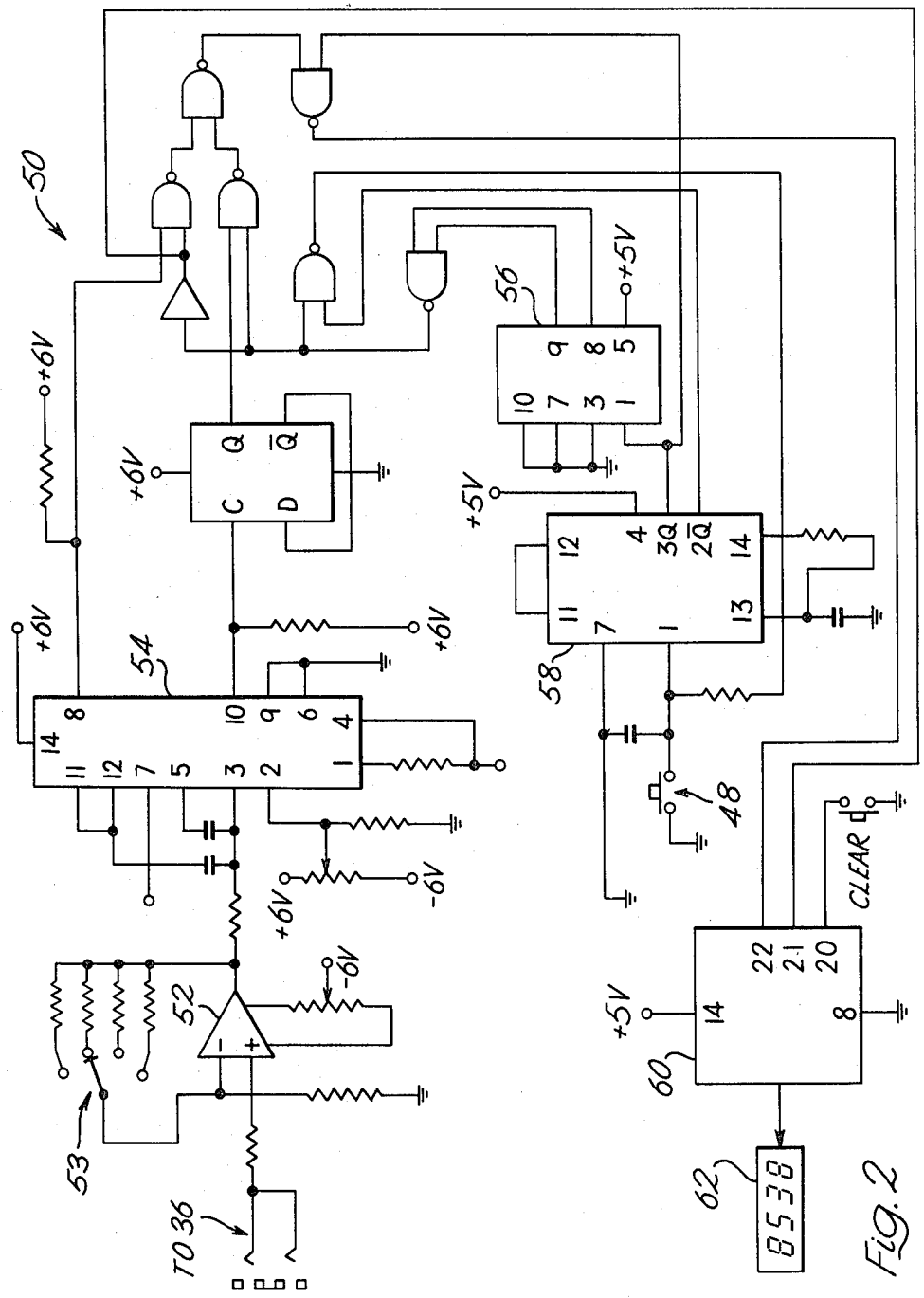
FIG. 2 illustrates a suitable electrical circuit for use in the explosimeter of FIG. 1.

The circuit 50 is shown in more detail in FIG. 2. The output from the oxygen meter 36 is connected to an operational amplifier 52 which supplies an amplified signal to a voltage-to-frequency converter 54; converter 54 is connected through a series of logic gates to a four digit counter driver 60 connected to a digital display 62. The switch 48 starts the operation of the counting part of the circuit. The precision timer 58 determines the timing periods which are counted by the decade counter 56 which in turn controls the mode of the four digit counter driver and the re-triggering of the precision timer 58. The oxygen meter 36 provides an input voltage proportional to oxygen concentration. The amplified input signal is accepted by the voltage-to-frequency converter (the range being determined by the gain of amplifier 52) and the analogue signal is converted to a pulse train whose frequency is linearly proportional to input voltage.

When the switch 48 is operated by insertion of the filter in the filter heater, the counter 60 starts counting the pulses (in the addition or count-up mode). After a precisely determined time T, the precision timer 58 in conjunction with the decade counter 56 causes the frequency from the converter 54 to be divided by 4, and switches the counting circuit to the subtraction or count-down mode. Re-triggering of the precision timer 58 is inhibited after five complete timing periods and this in turn prevents any further pulses reaching the four-digit counter driver 60.

Figure 3:
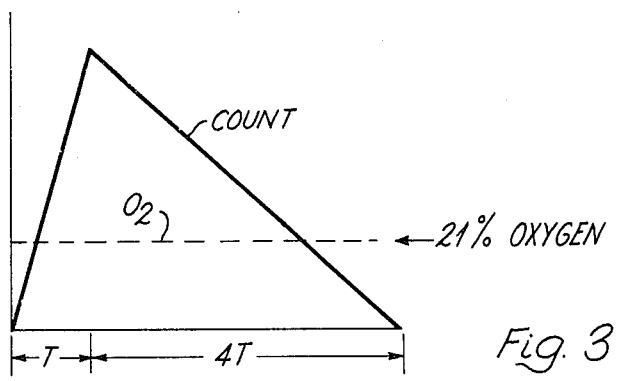
FIGS. 3 and 4 illustrate the counting mode of the explosimeter in the absence and presence of combustible material.

If the concentration of oxygen passing the sensor head 34 is constant, the number of pulses counted up in time T at voltage to frequency conversion rate x will equal the number of pulses counted down in time 4T at voltage to frequency conversion rate x/4. The display 62 will reach zero at the end of the fifth cycle. This is illustrated in FIG. 3 in which the dotted line shows oxygen concentration and the full line shows the pulse count.

Figure 4:
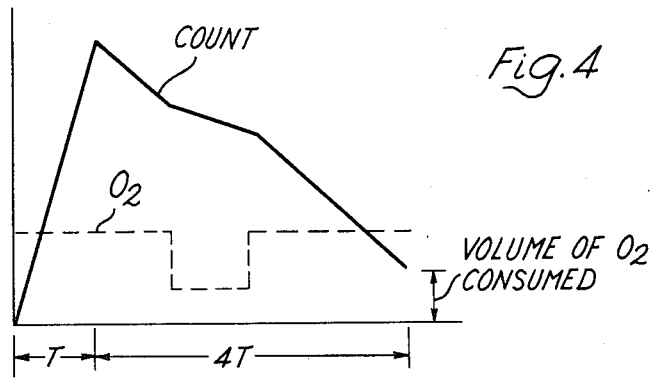

If the concentration of oxygen decreases due to the presence of combustible material, the display will contain a positive count at the end of the fifth cycle; this number is directly related to explosibility of the sample, provided the flow rate is kept constant. This is illustrated in FIG. 4. The drop in oxygen concentration (dotted line) is shown as a sharp change; this will not be the case in practice, but clearly illustrates the principle. Smooth changes in oxygen concentration merely alter the shape of the pulse count curve; the total effect is the same regardless of the mixing of the sample with the atmosphere, so long as the decrease due to all combustible material falls within the period 4T.

The final count in the counter 60 can, by suitable adjustment of the gain of amplifier 52, read directly as percentage stoichiometric. If the chemical composition of the fuel is known a switched gain 53 could be incorporated on amplifier 52 to give a direct reading in the display 62 of percentage lel for the particular fuel.

When a sample of an atmosphere is taken, the sampling rate must be sufficiently slow to capture large droplets in an aerosol. For example, for a 25 milliliter sample volume, a sampling rate of 75 milliliters per minute is appropriate.

It is essential for the reactor to be easily capable of oxidising all combustible material likely to be contained in the sample, remembering that concentrations far in excess of the upper explosive limit may be met. For a 25 milliliter sample, suitable dimensions are as follows; the tube 42 is of 0.6 centimeters internal diameter and the part forming the reactor 26 is 16 centimeters long and heated to 600° C. This provides an enormous oxidation capacity, considering the sample size, and the reactor catalyst is therefore not sensitive to inhibitors or poisons. The filter heater 24 is 7 centimeters long, heated to 300° C. T is 0.5 minutes so that integration takes place over 2.5 minutes at a flow rate of 220 milliliters per minute.

The advantages of the method according to the invention are that an unknown explosive gas can be sensed, that explosive mists, aerosols and vapour can be sensed; and that it is unaffected by changes in ambient oxygen concentration. In the inventive circuit, the final count is not seriously affected by electronic drift.

Figure 5:
FIG. 5 shows an alternative form of one part of the explosimeter.

A slight variation to the sampling part of the apparatus is shown in FIG. 5. A sample container 64 is connected by a demountable tube 66 to a chamber 68 containing a piston 70.

Initially, the piston is at the right-hand end of the chamber 68. The filter 74 connected to sample container 64 is inserted in the suspect atmosphere, the piston 70 is operated manually to draw a sample into container 64 through the filter. The tube 66 is then removed from container 64, and the junction sealed.

Since there is no air vent in container 64, the sample can be retained for long periods. When the sample is to be tested, the filter 74 is inserted in the filter heater (see FIG. 1) and the junction for tube 66 is opened so that the sample can be pumped into the reactor 26.

This device allows several samples of an atmosphere to be taken and tested later at a safe position.

I claim:

1. A method of sensing the explosibility of an atmosphere which may contain a combustible gas or vapour or mist or aerosol comprises drawing a known volume of the atmosphere through a filter on which any condensible material condenses and into a container;

in a safe environment, establishing a steady flow of oxygen-containing gas through a combustion chamber and past an oxygen sensor, heating the filter and drawing the gas sample from the container through the heated filter as part of the steady gas flow through the combustion chamber so that any combustible material is completely oxidised causing a decrease in oxygen concentration in the gas flow; and sensing and integrating any such decrease, and from the integrand determining the explosibility of the known volume.

2. A method according to claim 1 in which the combustible material is unknown and an approximate value of concentration as a percentage of the lower explosive limit is determined by multiplying the integrand by a factor approximately applicable to most combustible materials.

3. A method according to claim 1 in which the combustible material is known and a precise value of concentration expressed as as a percentage of the lower explosive limit is determined by multiplying the integrand by a factor applicable to the known combustible material.

4. A method according to claim 1 in which the oxygen-containing gas is the earth's atmosphere at a safe environment remote from the atmosphere under test and to which the sample container and filter are removed.

5. A method according to claim 1 in which the atmosphere initially contained in the combustion chamber and any connecting tubes is pumped past the oxygen sensor to provide the oxygen-containing gas in the steady flow preceding arrival of exhaust gas from the sample at the oxygen sensor.

6. A method according to claim 4 or claim 5 in which the atmosphere of the safe environment is drawn into and through the sample container at the same time as the sample is drawn through the heated filter, and then through the combustion chamber to provide the oxygen-containing gas in the steady flow succeeding arrival of exhaust gas from the sample at the oxygen sensor.

7. Apparatus for sensing the explosibility of an atmosphere which may contain a combustible gas or vapour or mist or aerosol comprises:

as a first part,
a container having a filter through which a sample of the atmosphere of known volume can be drawn into the container;
and as a second part,
a combustion chamber;
an oxygen sensor;

pump means for establishing a steady flow of oxygen-containing gas through the combustion chamber and past the oxygen sensor;

a filter heater into which the filter of the container can be inserted so that the pump means draws the gas sample from the container through the heated filter into the combustion chamber as part of the steady gas flow; and integrating means connected to the oxygen sensor.

8. Apparatus according to claim 7 in which the combustion chamber has an aperture through which the earth's atmosphere can be drawn before the filter is inserted in the filter heater.

9. Apparatus according to claim 7 or claim 8 in which a measure is made of the concentration of oxygen in the ambient atmosphere before the filter is inserted in the filter heater.

10. Apparatus according to claim 7 or claim 8, in which the container is provided with an aperture through which the earth's atmosphere can be drawn as the sample is pumped through the filter and into the combustion chamber.

11. Apparatus according to claim 7 or claim 8 in which the integrating means comprises first conversion means to convert the output signal from the oxygen sensor to a first pulse train having a frequency proportional to said output and at a first proportional rate; counting means to sum pulses in the first pulse train for a known first time period; second conversion means to convert the output signal to a second pulse train having a frequency proportional to said output and at a second proportional rate slower than the first rate by a known factor; switch means to cause the counting means to subtract pulses in the second pulse train from the sum of the pulses in the first pulse train for a second time period longer than the first time period by said known factor; and display means to display the pulse total.

* * * * *